United States Patent
Al-Ahmadi et al.

(10) Patent No.: US 9,221,774 B2
(45) Date of Patent: Dec. 29, 2015

(54) EPOXIDATION ON PROCESS WITH ADDED MODERATOR

(71) Applicant: Scientific Design Company, Inc., Little Ferry, NJ (US)

(72) Inventors: Hassan Eisa Al-Ahmadi, Washington Township, NJ (US); Ashok S. Padia, Glen Rock, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 13/655,000

(22) Filed: Oct. 18, 2012

(65) Prior Publication Data

US 2013/0096330 A1 Apr. 18, 2013

Related U.S. Application Data

(60) Provisional application No. 61/548,502, filed on Oct. 18, 2011.

(51) Int. Cl.
*C07D 301/08* (2006.01)
*C07D 301/03* (2006.01)
*C07D 301/04* (2006.01)

(52) U.S. Cl.
CPC ............ *C07D 301/03* (2013.01); *C07D 301/04* (2013.01)

(58) Field of Classification Search
CPC ... C07D 301/04; C07D 301/03; C07D 301/08
USPC ....................................................... 549/523
See application file for complete search history.

(56) References Cited

U.S. PATENT DOCUMENTS

| | | | |
|---|---|---|---|
| 2,279,469 | A | 4/1942 | Law et al. |
| 3,563,914 | A | 2/1971 | Wattimena |
| 3,702,259 | A | 11/1972 | Nielsen |
| 4,761,394 | A | 8/1988 | Lauritzen |
| 4,766,105 | A | 8/1988 | Lauritzen |
| 4,908,343 | A | 3/1990 | Bhasin |
| 5,011,807 | A | 4/1991 | Hayden et al. |
| 5,057,481 | A | 10/1991 | Bhasin |
| 5,099,041 | A | 3/1992 | Hayden et al. |

(Continued)

FOREIGN PATENT DOCUMENTS

| | | |
|---|---|---|
| CN | 1041591 A | 4/1990 |
| CN | 1599732 A | 3/2005 |

(Continued)

OTHER PUBLICATIONS

International Search Report and Written Opinion dated Mar. 6, 2013 issued in PCT/US2012/060482.

(Continued)

*Primary Examiner* — T. Victor Oh
(74) *Attorney, Agent, or Firm* — Scully, Scott, Murphy & Presser, P.C.

(57) ABSTRACT

A method for the epoxidation of an olefin comprising the steps of reacting a feed gas composition containing an olefin, oxygen, and a moderator having an optimal moderator concentration in the presence of an epoxidation catalyst at a first temperature and having a first selectivity; and increasing the optimal moderator concentration to a second moderator concentration and whereby the first selectivity is lowed to a second selectivity and the first temperature to a second temperature.

19 Claims, 3 Drawing Sheets

(56) References Cited

U.S. PATENT DOCUMENTS

| | | |
|---|---|---|
| 5,102,848 A | 4/1992 | Soo et al. |
| 5,187,140 A | 2/1993 | Thorsteinson et al. |
| 5,407,888 A | 4/1995 | Herzog et al. |
| 7,615,655 B2 | 11/2009 | Zhang et al. |
| 7,657,331 B2 | 2/2010 | Chipman et al. |
| 7,657,332 B2 | 2/2010 | Chipman et al. |
| 2007/0037991 A1 | 2/2007 | Rizkalla |
| 2010/0267972 A1 | 10/2010 | Zhang et al. |
| 2010/0267973 A1 | 10/2010 | Liu et al. |
| 2010/0267974 A1 | 10/2010 | Zhang et al. |
| 2010/0267975 A1 | 10/2010 | Habenschuss et al. |
| 2011/0152549 A1 | 6/2011 | Rizkalla et al. |

FOREIGN PATENT DOCUMENTS

| | | |
|---|---|---|
| EP | 0352850 A1 | 7/1989 |
| EP | 0352850 A1 | 1/1990 |
| GB | 1055147 | 1/1967 |
| RU | 2294327 C2 | 3/2005 |
| RU | 2296126 C2 | 3/2005 |
| WO | WO03044002 A1 | 5/2003 |
| WO | WO2004002972 A2 | 1/2004 |

OTHER PUBLICATIONS

European Search Report dated Apr. 23, 2015 received in a corresponding foreign application.

EPOXIDATION ON PROCESS WITH ADDED MODERATOR

CROSS REFERENCE TO RELATED APPLICATION

This application claims the benefit of U.S. Provisional Application Ser. No. 61/548,502, filed Oct. 18, 2011, the entire content and disclosure of which is incorporated herein by reference.

FIELD OF THE INVENTION

The present invention relates to a method for the epoxidation of an olefin in the presence of an added moderator.

BACKGROUND OF THE INVENTION

Though present in natural settings at minute quantities, ethylene oxide was first synthesized in a laboratory setting in 1859 by French chemist Charles-Adolphe Wurtz using the so-called "chlorohydrin" process. However, the usefulness of ethylene oxide as an industrial chemical was not fully understood in Wurtz's time; and so industrial production of ethylene oxide using the chlorohydrin process did not begin until the eve of the First World War due at least in part to the rapid increase in demand for ethylene glycol (of which ethylene oxide is an intermediate) as an antifreeze for use in the rapidly growing automobile market. Even then, the chlorohydrin process produced ethylene oxide in relatively small quantities and was highly uneconomical.

The chlorohydrin process was eventually supplanted by another process, the direct catalytic oxidation of ethylene with oxygen, the result of a second breakthrough in ethylene oxide synthesis, discovered in 1931 by another French chemist Theodore Lefort. Lefort used a solid silver catalyst with a gas phase feed that included ethylene and utilized air as a source of oxygen.

In the eighty years since the development of the direct oxidation method, the production of ethylene oxide has increased so significantly that today it is one of the largest volume products of the chemicals industry, accounting, by some estimates, for as much as half of the total value of organic chemicals produced by heterogeneous oxidation. Worldwide production in the year 2010 was about 22 million tons. About seventy percent of the ethylene oxide produced is further processed into ethylene glycol; about twenty percent of manufactured ethylene oxide is converted to other ethylene oxide derivatives and only a relatively small amount of ethylene oxide is used directly in applications such as vapor sterilization.

The growth in the production of ethylene oxide has been accompanied by continued intensive research on ethylene oxide catalysis and processing, which remains a subject of fascination for researchers in both industry and academia. Of particular interest in recent years has been the proper operating and processing parameters for the production of ethylene oxide using so-called "high selectivity catalysts", that is Ag-based epoxidation catalysts that contain small amounts of "promoting" elements such as rhenium and cesium.

Moderators, especially chloride moderators have long been used in the feed mixture for the gas phase production of ethylene oxide (see e.g., Law et al., U.S. Pat. No. 2,279,469, issued Apr. 14, 1942; U.K. Patent No. 1,055,147 issued Jan. 18, 1967, and Lauritzen, EPO Patent No. 0 352 850 B1, issued Jan. 19, 1994) and have been variously known also as "inhibitors", "anti-catalysts", and "promoters".

While the moderator's role was not fully understood in these prior publications, it is well understood that the moderator plays a key role in maintaining the catalyst's selectivity—the efficiency of the partial oxidation of ethylene to ethylene oxide. This is especially the case with respect to rhenium-containing, high selectivity catalysts because for these catalysts the selectivity versus moderator concentration tends to be very steep and thus, small changes away from the optimal moderator concentration (this is the moderator concentration that provides the maximum measured or observed selectivity for a given temperature and catalyst in-service age) can produce significant decline in selectivity performance.

In addition to selectivity, the activity curve—as measured by the catalyst temperature necessary to maintain constant production—is also sensitive to moderator concentration. More specifically, the catalyst temperature is inversely proportional to moderator concentration, which means that lower catalyst temperatures can be obtained by continually increasing the moderator concentration. Despite this evident trade-off between selectivity and activity, those involved in designing, supplying or operating ethylene oxide plants have devoted significant attention and resources in an attempt to regulate moderator concentration so that maximum selectivity is achieved, even if it necessarily also means that the catalyst is operated at higher temperature than could be obtained with higher moderator concentrations.

The most straightforward way of finding the optimal moderator concentration (and hence the maximum selectivity) involves simple manual adjustments to the reactor feed and operator parameters—when the reactor temperature or feed composition is changed the operators adjust the moderator concentrations in small increments until the maximum selectivity is achieved. Any further increase in moderator concentration will cause the selectivity to decline. As an alternative to manual adjusting moderator levels, techniques for automated and computer-controlled regulation of the moderator levels have also been previously proposed in the prior art. For example, U.S. Pat. Nos. 7,657,331 and 7,657,332 recite specific formulas and ratios to predict what the optimal moderator levels should be, making use of a "Q value" for calculating the correct chloride concentration. This Q value is the ratio of the total "effective" moderator to the total "effective" hydrocarbon. The "effective" hydrocarbon value is determined by multiplying the molar concentration for each species of hydrocarbon by a correction factor that (according to theory) accounts for the differences in the ability of the different hydrocarbons to remove/strip reaction moderator (especially chlorides) from the surface of the catalyst; while the "effective" moderator value is determined by multiplying the molar concentration for each species of moderator by a correction factor that (again according to theory) accounts for the number of "active species" present in a specific moderator. These correction factors are determined for each individual moderator and hydrocarbon by what is, apparently, a complicated process of experimental trial and error. Indeed, the process for determining these correction factors is not set out with specificity in the aforementioned patents nor any actual examples of the procedure presented. A similar approach for automatically adjusting moderator levels as applied to more diverse moderator blends can be seen in U.S. Pat. No. 7,615,655. As mentioned previously, both procedures are extremely complex to implement and are unlikely to have broad applicability in actual plant operation.

Thus, despite the development of these and other techniques designed to maximize selectivity there is still considerable dissatisfaction from some plants operators with the performance and requirements of high selectivity catalysts. Particularly it has been noted that the performance of high selectivity catalysts is less stable than the prior generation of high activity catalysts and thus have an apparently shorter service life. An additional problem is that less steam is generated during the operation of high selectivity catalysts, and because ethylene oxide/ethylene glycol plants rely on the steam generated in the reactor in order to supply steam needed in other parts of the process, it may be necessary to import steam from OSBL, outside battery limits, to ensure proper plant operation. This problem can be even further exacerbated in areas with insufficient utility capacity. Accordingly, there is a continuing need for methods for operating high selectivity catalysts in an ethylene oxide plant wherein such methods promote improved stability performance and provide for more consistent production of steam in the reactor.

BRIEF SUMMARY OF THE INVENTION

It has been discovered in the present invention that for many operators and in many ethylene oxide plants, the most efficient and economical operation of an ethylene oxide plant is obtained when, after an optional conditioning period, the start of run selectivity is lowered below the maximum selectivity by increasing the moderator concentration.

The present invention relates to a method for the epoxidation of an olefin comprising the steps of reacting a feed gas composition containing an olefin, oxygen, and a moderator having an optimal moderator concentration in the presence of an epoxidation catalyst at a first temperature and having a first selectivity; and increasing the optimal moderator concentration to a second moderator concentration and whereby the first selectivity is lowered to a second selectivity and the first temperature to a second temperature.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
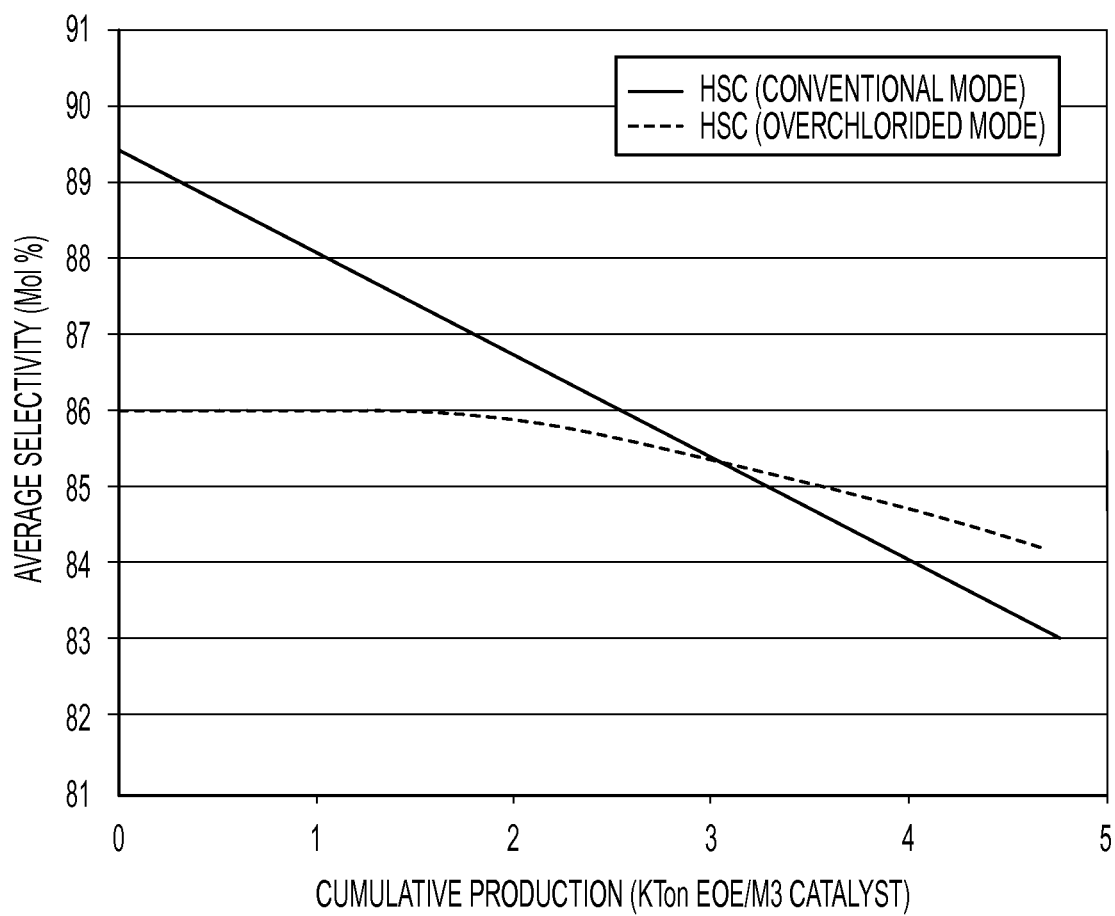
FIG. 1 is a graph for an ethylene oxide catalyst showing theoretical curves for operation according to the prior art and according to the present invention.

All parts, percentages and ratios used herein are expressed by volume unless otherwise specified. All documents cited herein are incorporated by reference.

By "optimal moderator concentration" it is meant the moderator concentration that provides the maximum measured or observed selectivity at a given temperature and at a specific catalyst age.

The present invention is directed to the gas phase epoxidation of an olefin to form an olefin oxide by contacting a Re-containing silver-based catalyst in a reactor with a feed that contains at least oxygen, an olefin, and a moderator. It has been discovered in the present invention that improved catalyst performance over the useful life of the catalyst as well as plant economics and operation can be obtained by operating the catalyst at selectivities below the maximum selectivity and that this can be done by increasing the moderator concentration to concentrations higher than optimal moderator concentration. As described above, this technique is contrary to conventional practice: typically plant operators have focused intensely on finding the specific moderator concentration that maximizes selectivity which then served as the start-of-run selectivity. Then, as the catalyst ages during service, the moderator concentration is continually adjusted in order to maintain maximum selectivity. However, the problem with operating the catalyst this way is that it essentially overemphasizes the "instantaneous" selectivity: the highest selectivity that can be obtained at the specific service age of the catalyst. However, what is more important to plant performance and economics is the "average" selectivity over the life of the catalyst. By seeking to maximize instantaneous selectivity, the catalyst is run at higher temperatures than is necessary to sustain productivity. These higher temperatures accelerate the aging of the catalyst and may lead to lower average selectivities when measured over the entire length of the run. It is important to note that the present invention is not meant to replace conventional high selectivity catalyst operating practice or techniques at all ethylene oxide plants. The present invention is, however, a particularly effective and efficient process for some plants and plant operators.

In contrast to the prior art technique of managing a high selectivity catalyst, in the present invention the emphasis is on maintaining a lower catalyst temperature—essentially sacrificing higher instantaneous selectivity for improved average selectivity and higher activity. This is done by increasing the moderator concentration above the optimal moderator concentration which results in lower catalyst selectivity and higher activity (by higher activity it is meant that the temperature of the catalyst to maintain constant production can be lowered). Under these conditions it can be said that the catalyst is "overmoderated". As mentioned above, by overmoderating one is sacrificing improved selectivity in order to increase activity (and thus lower the catalyst temperature), and while this is counter to prior art teachings it has at least two technical advantages.

First, maintaining the catalyst at lower temperatures may result in overall superior selectivity performance because, as mentioned above, the catalyst is more stable and "ages" more slowly. Thus, while the initial start-of-run selectivity is lower, the average selectivity over the entire service life of the catalyst is higher. This is shown graphically in FIG. 1, which shows two hypothetical curves of the selectivity versus catalyst age for two catalyst runs, one operated according to conventional practice and one according to the present invention (shown in units of EOE, ethylene oxide equivalents, produced per volume of catalyst). Each point on the curves represents the average selectivity for the run up until that point. So that when the catalysts have each produced 0.5 kT EOE/$m^3$ the average selectivity of the high selectivity catalyst operated according to conventional practice is about 88.75%—which is higher than the average selectivity up to the point of the catalyst operated according to the present invention, which is about 86%. However, by the end of the run things have changed considerably. At 4.5 kT EOE/$m^3$ the selectivity average over the entire course of the run for the high selectivity catalyst operated according to conventional practice is about 83.5%—about 1% lower than the average selectivity of 84.5% that is obtained by the catalyst operated according to the present invention.

A second technical effect and advantage relates to the increased production of steam in the reactor at lower selectivities. Steam is important because it is especially envisioned that the present invention will be practiced as the vapor-phase oxidation of ethylene over a silver-based catalyst in a fixed-bed tubular boiling-water reactor with the catalyst loaded inside the fixed-bed tubes and the water/steam coolant on the shellside. The reactions taking place over the catalyst bed are exothermic—producing a significant amount of heat that is absorbed and regulated by the water and steam mixture on the shellside and the steam produced thereby as a result of the boiling of water on the shellside is important because this steam is needed elsewhere in the plant—especially in the hydrolysis of ethylene oxide to form monoethylene glycol and other heavier glycols. If a plant is not capable of producing sufficient steam in the reactor then steam must be imported from OSBL—this not only undermines the economics and efficiency of the process but for some plant operators is not even possible because of a lack of utility infrastructure in the area surrounding the plant. Both the product reaction (to ethylene oxide) and the by-product reaction (to form $CO_2$) are exothermic—but the by-product reaction is over sixteen times more exothermic so that by lowering the selectivity, the result is that more of the ethylene and oxygen are consumed in the by-product reaction thus generating a higher heat of reaction to increase steam make in the reactor—this steam can then be used elsewhere in the plant without having to import steam.

By contrast, when high selectivity catalysts are operated according to conventional processes, the economics and operation of the process can be seriously inefficient when it comes to steam production because they exhibit a very steep steam production curve (although this varies significantly based on the specific circumstances of the plant and its operation). So for example, at the beginning of the catalyst run, when the catalyst is fresh, the selectivity is relatively high and the reaction is less exothermic because the product reaction strongly predominates over the more exothermic by-product reaction—thus, a relatively low quantity of steam is generated, meaning as mentioned above that steam may have to be imported from OSBL. However, under the conventional regime as the catalyst ages, the proportion of the by-product reaction increases relative to the product reaction so that the overall reaction becomes more exothermic thus generating increasingly larger quantities of steam. Thus in the conventional process the steam make is significantly unbalanced—when fresh catalyst is used the amount of steam generated is so low that additional steam may have to be imported while with aged catalysts an amount of steam in excess of requirements may be produced possibly requiring special procedures and equipment for the operator to handle and dispose the excess steam.

It should be noted that although the above description is specified with respect to the specific boiling water reactor configuration, any conventional fixed bed reactor system may be suitable for practicing the present invention.

The process of the present invention will be described in greater detail after a brief discussion of the silver catalyst to be used in the process.

Silver-Based Epoxidation Catalyst

The silver-based epoxidation catalyst includes a support, and at least a catalytically effective amount of silver or a silver-containing compound; also optionally present is a promoting amount of rhenium or a rhenium-containing compound; also optionally present is a promoting amount of one or more alkali metals or alkali-metal-containing compounds. The support employed in this invention may be selected from a large number of solid, refractory supports that may be porous and may provide the preferred pore structure. Alumina is well known to be useful as a catalyst support for the epoxidation of an olefin and is the preferred support. The support may comprise materials such as alpha-alumina, charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics and combination thereof. The support may comprise at least about 95 wt. % alpha-alumina; preferably, at least about 98 wt. % alpha-alumina. The remaining components may include inorganic oxides other than alpha-alumina, such as silica, alkali metal oxides (e.g., sodium oxide) and trace amounts of other metal-containing or non-metal-containing additives or impurities.

Regardless of the character of the support used, it is usually shaped into particles, chunks, pieces, pellets, rings, spheres, wagon wheels, cross-partitioned hollow cylinders, and the like, of a size suitable for employment in a fixed-bed epoxidation reactor. The support particles will preferably have equivalent diameters in the range from about 3 mm to about 12 mm, and more preferably in the range from about 5 mm to about 10 mm. Equivalent diameter is the diameter of a sphere having the same external surface (i.e., neglecting surface within the pores of the particle) to volume ratio as the support particles being employed.

Suitable supports are available from Saint-Gobain Norpro Co., Sud Chemie AG, Noritake Co., CeramTec AG, and Industrie Bitossi S.p.A. Without being limited to the specific compositions and formulations contained therein, further information on support compositions and methods for making supports may be found in U.S. Patent Publication No. 2007/0037991.

In order to produce a catalyst for the oxidation of an olefin to an olefin oxide, a support having the above characteristics is then provided with a catalytically effective amount of silver on its surface. The catalyst is prepared by impregnating the support with a silver compound, complex or salt dissolved in a suitable solvent sufficient to cause deposition of a silver-precursor compound onto the support. Preferably, an aqueous silver solution is used.

A promoting amount of a rhenium component, which may be a rhenium-containing compound or a rhenium-containing complex may also be deposited on the support, either prior to, coincidentally with, or subsequent to the deposition of the silver. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Other components which may also be deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of support, silver, alkali metal promoter(s), rhenium component, and optional additional promoter(s) of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof. Most preferably the transition metal comprises an element selected from Groups IVA, VA or VIA of the Periodic Table of the Elements. Preferred transition metals that can be present include molybdenum, tungsten, chromium, titanium, hafnium, zirconium, vanadium, tantalum, niobium, or combinations thereof.

The amount of alkaline earth metal promoter(s) and/or transition metal promoter(s) deposited on the support is a promoting amount. The transition metal promoter may typically be present in an amount from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the metal. The catalyst may further comprise a promoting amount of one or more sulfur compounds, one or more phosphorus compounds, one or more boron compounds, one or more halogen-containing compounds, or combinations thereof.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described, for example, in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various promoters can be employed.

After impregnation of the support with the silver-containing compound, i.e., a silver precursor, a rhenium component, an alkali metal component, and the optional other promoters, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range from about 200° C. to about 600° C. at a pressure in the range from about 0.5 to about 35 bar. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Further information on catalyst manufacture may be found in the aforementioned U.S. Patent Publication No. 2007/0037991.

Epoxidation Process

The epoxidation process may be carried out by continuously contacting an oxygen-containing gas with an olefin, preferably ethylene, in the presence of the previously-described catalyst. Oxygen may be supplied to the reaction in substantially pure molecular form or in a mixture such as air. By way of example, reactant feed mixtures may contain from about 0.5% to about 45%, preferably about 5% to about 30% of ethylene and from about 3% to about 15% oxygen, with the balance comprising comparatively inert materials including such substances as carbon dioxide, water, inert gases, other hydrocarbons, and the reaction moderators described herein. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum.

Also present in the reaction, as previously mentioned, are one or more moderators non-limiting examples of which include organic halogen-containing compounds such as $C_1$ to $C_8$ halohydrocarbons; especially preferred are chloride-containing moderators such as methyl chloride, ethyl chloride, ethylene dichloride, vinyl chloride or mixtures thereof. Controlling moderator concentration level is particularly important with rhenium-containing catalysts. As mentioned previously the present invention also makes use of a specific moderator control system.

A usual method for the ethylene epoxidation process comprises the vapor-phase oxidation of ethylene with molecular oxygen, in the presence of the inventive catalyst, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-53 feet long filled with catalyst. Such reactors include a reactor outlet which allows the olefin oxide, un-used reactants, and byproducts to exit the reactor chamber.

In actual service, it is typical (especially for a high selectivity catalyst, HSC) to condition the catalyst in a "conditioning", "initiation", or "start-up" process before reaching typical operating conditions and producing commercial scale quantities of ethylene oxide, EO, it is typical (especially for HSC) to condition the catalyst in a "conditioning", "initiation", or "start-up" process. (Conditioning is optional in the present invention.) The present invention is not specific to any particular conditioning or start-up process, rather the present invention makes use of the discovery that, when properly operated, it is preferred to operate the catalyst at lower selectivities than are necessarily obtainable. However, speaking generally, the catalyst is contained within a specific temperature range such as about 240° C. to about 280° C. This temperature range is essentially the active and commercially relevant temperature range for a high selectivity catalyst. Generally, temperatures below 240° C. are too low for the catalyst to become active and produce ethylene oxide at commercial scale. Accordingly, the present invention does not apply to catalysts that become active at temperatures below 240° C. On the upper end of the scale, 280° C. is about the highest temperature at which most EO plants can operate at and is about the highest temperature at which the catalyst can effectively perform. At levels above 280° C. there is significant migration of silver and active sites effectively destroying catalytic performance. Typical operating conditions for the ethylene epoxidation process involve temperatures in the range from about 180° C. to about 330° C., and preferably, from about 200° C. to about 325° C., and more preferably from about 225° C. to about 280° C. As mentioned above, the moderator control system described in the present invention operates most effectively within the temperature range of about 240° C. to about 280° C.

Figure 2:
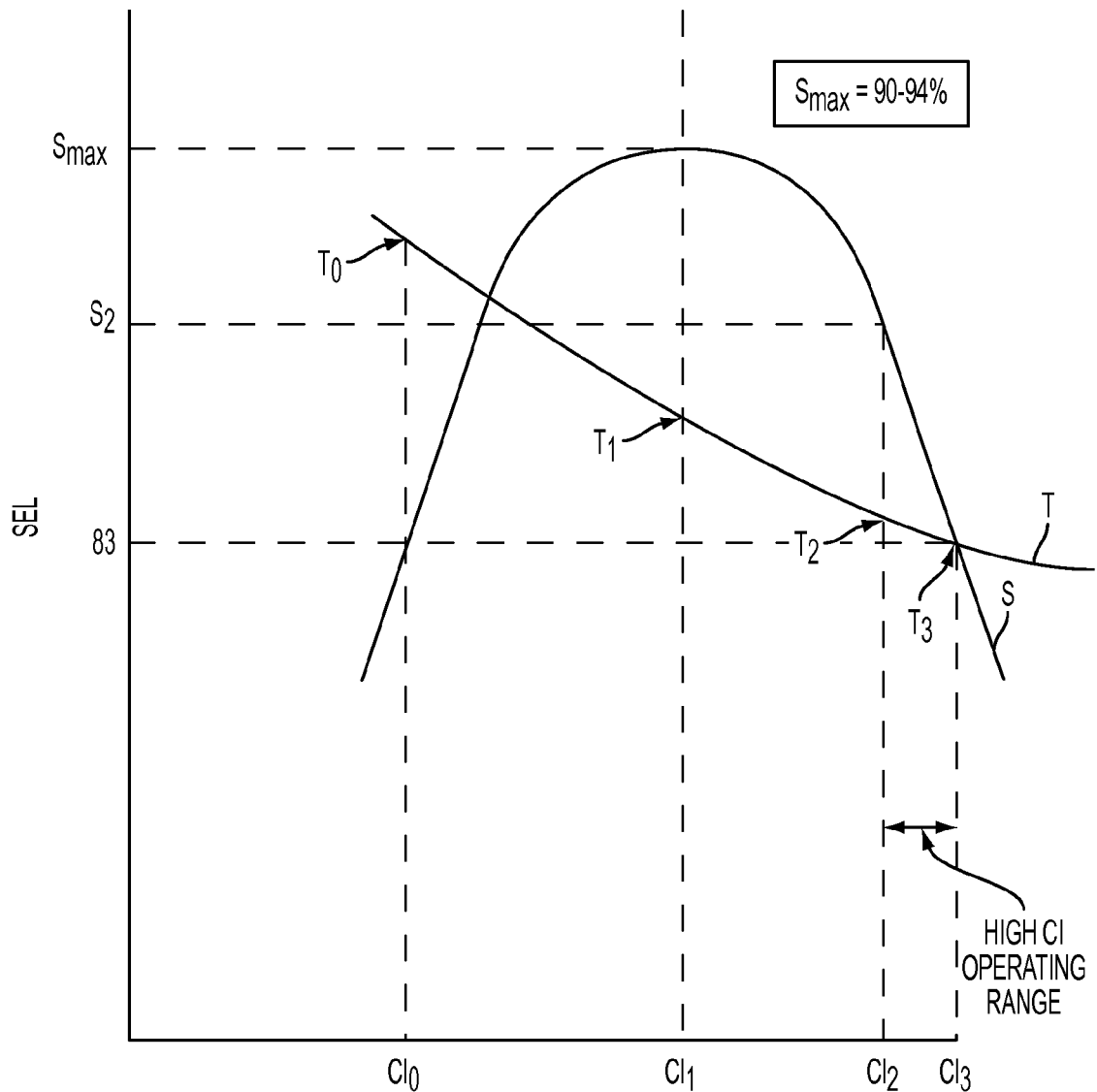
FIG. 2 is a graph for an ethylene oxide catalyst showing the activity and selectivity versus moderator concentration during proposed catalyst operation according to the present invention.

In the present invention, the operator may decide to implement the moderator control procedure at a temperature at or in excess of 240° C. After an optional conditioning step, the first step for an operator under the present invention is to determine the optimal moderator concentration, i.e., the moderator concentration that produces the highest measured or observable selectivity. This may be done by any suitable means. For example, the incremental approach mentioned above may be used in which the optimal moderator concentration is determined manually by trial and error; so that when the reactor temperature of feed compositions is changed the operator adjusts the moderator concentration in small increments until it appears that the maximum selectivity has been achieved. This may require both increasing and decreasing chlorides around a selectivity peak until the maximum selectivity is determined. After the optional conditioning step the operator may simply start increasing the moderator concentration with accompanying effects on selectivity and temperature as shown in FIG. 2. In FIG. 2 it can be seen that as the moderator (in the case the moderator is indicated by total chloride concentration) increases, the temperature decreases and the selectivity increases. As practiced according to the present invention, the operator continues to increase the moderator (e.g., total chlorides) incrementally by small amounts until the observed selectivity maximum (also known in the present application as "first selectivity") of $S_{max}$ is reached at a first temperature, $T_1$ at the optimal moderator concentration designated $Cl_1$. $S_{max}$ is the not necessarily the maximum selectivity of the catalyst, but rather the high measured or observed selectivity value $S_{max}$ is preferably within the range of about 87% to about 92%. At this point, the conventional process would be to stop adding moderator and to attempt to hold at the selectivity at approximately $S_{max}$ or at least as high as possible. However, as practiced by the present invention, the moderator concentration is increased to $Cl_2$ and thereby the selectivity is lowered to a second selectivity, $S_2$ and the temperature to a second temperature $T_2$. The amount by which the maximum selectivity is lowered to the second selectivity, $S_2$, value is ultimately the choice of the operator, but the amount that maximum selectivity is lowered should be sufficiently large so that second temperature $T_2$ is low enough to ensure that the stability of the catalyst may be improved as previously described. The temperature difference $T_1-T_2$ is 0.5° C. to about 20° C., preferably about 1° C. to about 15° C., most preferably about 2° C. to about 10° C. As discussed above the typical operating temperature range for high selectivity catalyst is between 240° C. to about 280° C. and so the temperatures $T_1$ and $T_2$ should be in this range.

It is envisioned that in the present invention the selectivity difference $S_{max}-S_2$ is about 0.5 to 6%, preferably 1 to 5%, more preferably 2 to 4%. For the remainder of the catalyst life the operator should then attempt to maintain selectivity as high as possible using conventional techniques, but not to exceed 93% or more preferably about 85% to about 89%.

As mentioned above, deliberating lowering selectivity within the aforementioned amount at the start of the run has the technical effect of lowering the temperature sufficiently to reduce catalyst aging and thus promote catalyst stability and life. The result of this will produce overall superior average selectivity. Additionally, this will result in improved steam utilization.

Figure 3:
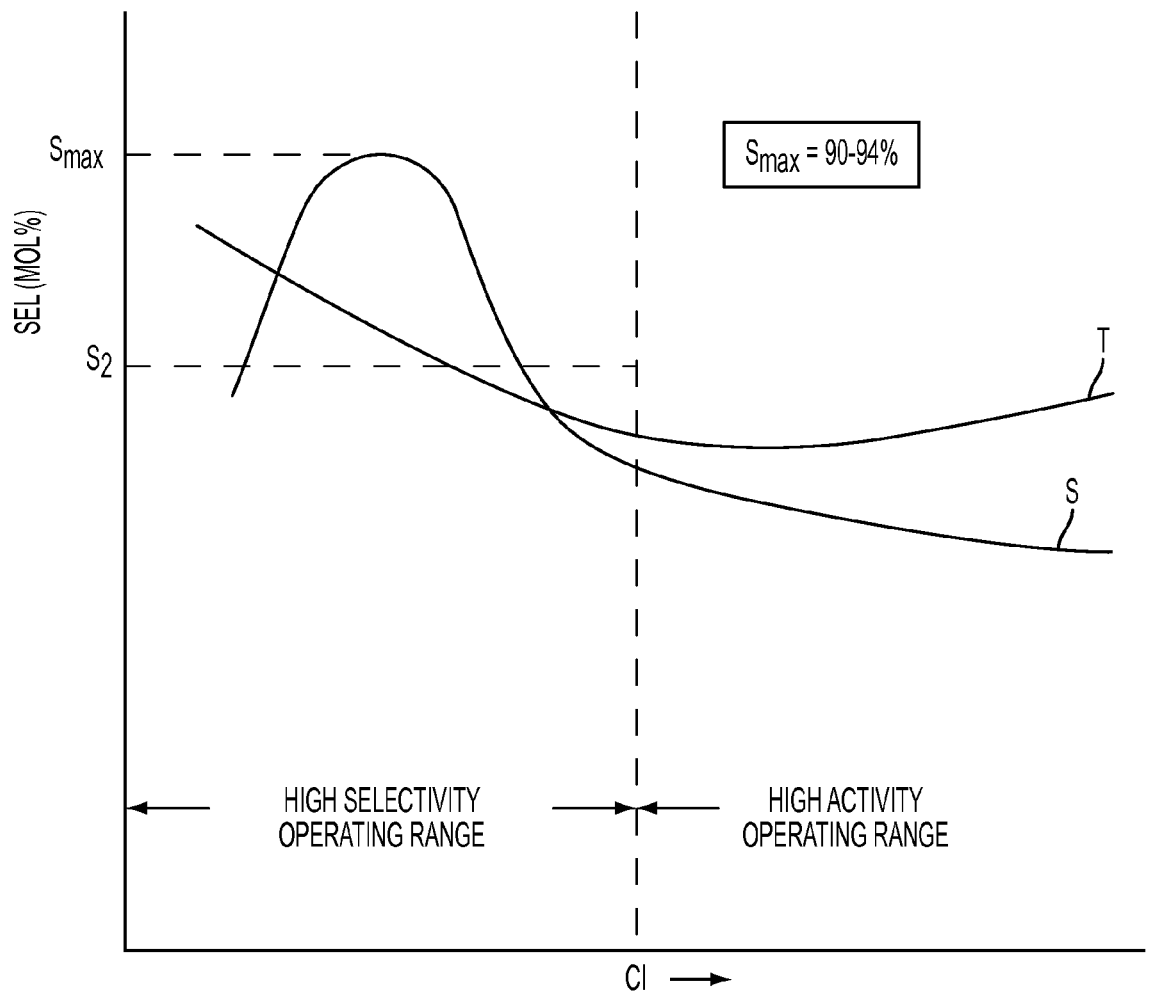
FIG. 3 is a graph for an ethylene oxide catalyst showing the activity and selectivity versus moderator concentration illustrating the transition from high selectivity operation to high activity operation.

As mentioned above, in the present invention a sufficient amount of moderator is added to lower selectivity from $S_{max}$ to $S_2$. When chloride-containing moderators are being used the increase in total chlorides (i.e., difference between second chloride concentration and optimal moderator concentration, $Cl_2-Cl_1$) necessary to lower the selectivity from $S_{max}$ to $S_2$ will be from about 1 ppm to about 10 ppm, preferably from about 1 ppm to about 7 ppm. It is important that the amount of moderator be carefully controlled to prevent too much from being used, because above a certain chloride concentration, a high selectivity catalyst will operate as a high activity catalyst instead. In a high activity catalyst regime, activity decreases with increase chloride concentration. This is illustrated in FIG. 2, where above the third chloride concentration $Cl_3$, both activity and selectivity decrease with increasing chloride concentration. This behavior is also shown across a broader scale in FIG. 3.

Alternatives to this manual or incremental approach in determining $S_{max}$, $S_1$, $T_1$, and $T_2$ include the automated or calculation techniques also mentioned above. Regardless of the technique adopted, the optimal moderator concentration is determined by the operator based on their own specific parameters and circumstances and as above with respect to specific start-up or initiation processes, determining the first moderator concentration for desired performance levels is done according to techniques known by persons of ordinary skill in the art.

In another acceptable alternative embodiment, the operator does not determine the maximum selectivity value and the optimal moderator concentration based on observing or measuring selectivity, temperature or moderator concentration levels or by an analysis of the catalyst's operating parameters. Rather, instead the operator, possibly with the technical assistance of the catalyst manufacturer, selects a priori the $S_{max}$ for the catalyst based on previous plant operating experience and in consultation with the catalyst manufacture. The additional values $S_2$, $T_1$, and $T_2$ are determined as described above.

The previously-described catalysts have been shown to be particularly selective for oxidation of ethylene with molecular oxygen to ethylene oxide especially at high ethylene and oxygen conversion rates. The conditions for carrying out such an oxidation reaction in the presence of the catalysts of the present invention broadly comprise those described in the prior art. This applies to suitable temperatures, pressures, residence times, diluent materials, moderating agents, and recycle operations, or applying successive conversions in different reactors to increase the yields of ethylene oxide. The use of the present catalysts in ethylene oxidation reactions is in no way limited to the use of specific conditions among those which are known to be effective.

For purposes of illustration only, the following are conditions that are often used in current commercial ethylene oxide reactor units: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production rate (work rate) of 7-20 lbs. EO/cu.ft. catalyst/hr and a change in ethylene oxide concentration, $\Delta EO$, of from about 1.5% to about 4.5%. The feed composition in the reactor inlet after the completion of start-up and during normal operation typically comprises (by volume %) 1-40% ethylene, 3-12% $O_2$; 0.2% to 10%, preferably 0.2% to 6%, more preferably 0.2% to 5% of $CO_2$; 0-5% ethane, an amount of one or more chloride moderators, which are described herein; and the balance of the feed being comprised of argon, methane, nitrogen or mixtures thereof.

EXAMPLE

The invention will now be described in more detail with respect to the following non-limiting example.

A 6.5 gram rhenium-containing catalyst pellet was prepared then crushed, ground and screened to provide a sample of 14-18 mesh particles. 6.5 grams of the material were then charged to a ¼ outer diameter heated microreactor with automated chloride control. The catalyst sample was conditioned first by heating the reactor to 245° C. for 100 hours with a feed concentration of about 1.1 ppm (by volume) ethyl chloride, 8% $C_2H_4$, 7% $O_2$, 2% $CO_2$, balance $N_2$, at a WHSV of 4760. After the completion of 100 hours of conditioning, the selectivity was found to be 86%. The ethylene concentration was then raised to 25% and the run continued with a productivity of 2.2 $\Delta EO\%$ and chloride concentrations were lowered to as low as 0.5 ppm in order to increase selectivity—selectivity did in fact increase to 89% (and thus designated as $S_{max}$). This selectivity value was held constant for 48 hours at which point overmoderating as taught by the present invention was started by gradually increasing the chloride concentration of a period of over 3 days to 1.5 ppm and then 2.6 ppm at which point selectivity fell to around 87%. This was determined to be the $S_2$ temperature and chlorides were adjusted to maintain it.

While the present invention has been particularly shown and described with respect to various embodiments thereof, it will be understood to those skilled in the art that the foregoing and other changes in forms and details may be made without departing from the spirit and scope of the present invention. It is therefore intended that the present invention not be limited to the exact forms and details described and illustrated, but fall within the scope of the appended claims.

We claim:
1. A method for the epoxidation of an olefin comprising:
   reacting a feed gas composition containing an olefin, oxygen, and a moderator having an optimal moderator concentration in the presence of an epoxidation catalyst at a first temperature and having a first selectivity; and
   increasing the optimal moderator concentration to a second moderator concentration, wherein during said increasing the first selectivity is lowered to a second selectivity, the first temperature is lowered to a second temperature, and a productivity is obtained such that a change in ethylene oxide concentration, $\Delta EO$, is from about 1.5 % to about 4.5 %.
2. The method of claim 1, wherein a difference between the first selectivity and the second selectivity is about 0.5 to 5 %, and the first selectivity is about 87 % to about 92 %.
3. The method of claim 2, wherein a difference between the first selectivity and the second selectivity is about 1 to 4 %.
4. The method of claim 2, wherein a difference between the first selectivity and the second selectivity is about 2 to 3 %.
5. The method of claim 1, wherein a difference between the first temperature and the second temperature is about 0.5 ° C. to about 20 ° C.
6. The method of claim 5, wherein the difference between the first temperature and the second temperature is about 1 ° C. to about 15 ° C.
7. The method of claim 5, wherein the difference between the first temperature and the second temperature is about 2 ° C. to about 10 ° C.
8. The method of claim 1, wherein a difference between the second moderator concentration and the optimal moderator concentration is about 1 ppm to about 10 ppm.

9. The method of claim 8, wherein a difference between the second moderator concentration and the optimal moderator concentration is about 1 ppm to about 7 ppm.

10. The method of claim 1, wherein the first temperature and the second temperature are within a range of about 240° C. to about 280° C.

11. The method of claim 1, where the feed gas composition contains about 1% to about 40% of ethylene, about 3% to about 12% oxygen, and about 0.2% to about 10% $CO_2$.

12. The method according to claim 1, wherein the moderator is a chloride-containing moderator.

13. The method according to claim 1, wherein the moderator is a selected from the group consisting of methyl chloride, ethyl chloride, ethylene dichloride and vinyl chloride.

14. A method for the epoxidation of an olefin comprising:
conditioning a rhenium-containing silver based ethylene oxide catalyst in the presence of feed gas composition containing an olefin having a first concentration, oxygen and a moderator having a first concentration to obtain a first selectivity;
increasing the first selectivity of said catalyst by increasing the first concentration of the olefin in said feed gas composition to a second concentration and decreasing the first concentration of said moderator to a second concentration;
holding said second selectivity for a period of time; and
increasing the second concentration of said moderator to a third concentration, wherein during said increasing the second concentration, the second selectivity is lowered to a third selectivity.

15. A method for the epoxidation of an olefin comprising:
providing a rhenium-containing epoxidation catalyst into an epoxidation reactor;
adding a feed gas containing an olefin, oxygen, and a moderator to said epoxidation reactor;
determining an optimal concentration of the moderator within the feed gas to obtain a selectivity maximum in a range from 87% to 92% and at a first temperature by adjusting moderator concentration; and
increasing the concentration of the moderator to a second concentration that is higher than the optimal concentration, wherein during said increasing the selectivity maximum is lowered to a second selectivity, the first temperature is lowered to a second temperature.

16. The method of claim 15, wherein a difference between the selectivity maximum and the second selectivity is from 0.5 to 5%.

17. The method of claim 16, wherein a difference between the first temperature and the second temperature is about 0.5° C. to about 20° C.

18. The method of claim 17, wherein a difference between the second concentration and the optimal concentration is about 1 ppm to about 10 ppm.

19. The method of claim 18, wherein said increasing the concentration of the moderator provides a productivity such that a change in ethylene oxide concentration, AEO, is from about 1.5% to about 4.5%.

* * * * *